US00PP23622P3

(12) United States Plant Patent
Tuinier

(10) Patent No.: US PP23,622 P3
(45) Date of Patent: May 21, 2013

(54) ***GASTERIA* PLANT NAMED 'WT10'**

(50) Latin Name: *Gasteria hybrid*
Varietal Denomination: WT10

(75) Inventor: Wander Tuinier, Krimpen a/d IJssel (NL)

(73) Assignee: Wander Tuinier BV, Krimlen A/D Ijssel (NL)

( * ) Notice: Subject to any disclaimer, the term of this patent is extended or adjusted under 35 U.S.C. 154(b) by 153 days.

(21) Appl. No.: 12/925,502

(22) Filed: Oct. 21, 2010

(65) Prior Publication Data

US 2012/0102612 P1 Apr. 26, 2012

(51) Int. Cl.
*A01H 5/00* (2006.01)

(52) U.S. Cl.
USPC ..... Plt./373

(58) Field of Classification Search ..... Plt./263.1, Plt./373, 372
See application file for complete search history.

*Primary Examiner* — Kent L Bell
(74) *Attorney, Agent, or Firm* — Mark P. Bourgeois

(57) ABSTRACT

A new and distinct *Gasteria* hybrid cultivar named 'WT10' is disclosed, characterized by foliage with a strong green color and grey green tubercles. The overall plant form is a very evenly growing whorled rosette. The new variety is a *Gasteria* hybrid, typically produced as an ornamental plant.

1 Drawing Sheet

Latin name of the genus and species: *Gasteria* hybrid.
Variety denomination: 'WT10'.

BACKGROUND OF THE INVENTION

The new cultivar was discovered as a seedling, in a population of open pollinated unnamed *Gasteria* hybrid plants. The exact seed and pollen parents are unknown. 'WT10' was selected by the inventor, Wander Durk Tuinier, a citizen of the Netherlands, as a single plant. The new variety was discovered April 2008, in a commercial greenhouse in Swellendam, South Africa.

Asexual reproduction of the new cultivar 'WT10' was first performed in South Africa, at a commercial laboratory by tissue culture in September 2008. 'WT10' has since produced many generations and has shown that the unique features of this cultivar are stable and reproduced true to type.

SUMMARY OF THE INVENTION

The cultivar 'WT10' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'WT10'. These characteristics in combination distinguish 'WT10' as a new and distinct *Gasteria* cultivar:

1. Strong green foliage color with small grey-green dots.
2. Distinctive evenly whorled rosetting plant form.

COMMERCIAL COMPARISON

The closest comparison cultivar is *Gasteria* 'Green Star' (not patented). 'WT10' is distinguishable from 'Green Star' by the following characteristics: 1. 'WT10' has a growth habit that is more spreading in comparison to the habit of 'Green Star'. The growth habit of 'Green Star' is more upright than the habit of 'WT10'.

BRIEF DESCRIPTION OF THE PHOTOGRAPH

The accompanying photograph in FIG. 1 illustrates in full color a typical plant of 'WT10' indoors in the Netherlands. This plant is approximately 30 months old, shown in a 12.5 cm pot. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Colour Chart, except where general terms of ordinary dictionary significance are used. The following observations and measurements describe 'WT10' plants in a commercial greenhouse in Kimpen aan de Ijssel, the Netherlands. Temperatures ranged from 20° C. to 22° C. night and day. No artificial light, photoperiodic treatments or chemical treatments were given to the plants. Measurements and numerical values represent averages of typical plant types.

Botanical classification: *Gasteria* hybrid 'WT10'.

PROPAGATION

Time to initiate roots: About 21 days at approximately 22-24° C.
Root description: Fibrous.
Propagation method: Tissue culture.

PLANT

Growth habit: Rosulate compact succulent.
Age of plant described: Approximately 30 months.

Container size: 12.5 cm diameter.

Height: Approximately 7.7 cm to top of highest leaf, measured from the soil line.

Plant spread: Approximately 15.5 cm.

Growth rate: Slow.

Branching characteristics: No lateral branches, whole plant consists of a single rosette; new rosettes (average: 2) grow from the base.

FOLIAGE

Leaf:

*Arrangement*.—Rosette.

*Average length*.—Approximately 7.0 cm.

*Average width*.—Approximately 2.7 cm.

*Average leaf thickness*.—Approximately 0.4 cm at thinnest section, near margin. Approximately 0.8 cm in thickest section, near center of leaf.

*Shape of blade*.—Lanceolate.

*Apex*.—Apiculate with a short aristate tip.

*Base*.—Broad cuneate.

*Margin*.—Denticulate.

*Texture of top surface*.—Tuberculate.

*Texture of bottom surface*.—Tuberculate. Tubercule diameter: Average range from 0.15 cm to 0.25 cm.

*Quantity of leaves per plant*.—Approximately 35.

*Color*.—Young foliage upper side: Near RHS Green N137A tubercles near RHS Greyed-Green 192D, base of leaf near attachment point near RHS 161B. Young foliage under side: Near RHS Green 139A, tubercles near RHS Greyed-Green 192D, base of leaf near attachment point near RHS 161B. Mature foliage upper side: Near RHS Green 139A, tubercles near RHS Grey-Green 192D, base near point of attachment near RHS White N155C. Mature foliage under side: Near RHS Green 139A tubercles near RHS Greyed-Green 192D, base near point of attachment near RHS N155C.

*Venation*.—Type: Linear. Venation color upper side: Near RHS Green 139A, base venation RHS White N155C. Venation color under side: Near RHS Green 139A, base venation RHS White N155C.

FLOWER

No flowers observed to date:

OTHER CHARACTERISTICS

Seeds and fruits: Not observed to date.

Disease/pest resistance: Neither resistance nor susceptibility to the normal pathogens of *Gasteria* has been observed.

Temperature tolerance: Tolerates temperatures from approximately 3° C. to at least 40° C.

Drought tolerance: Drought tolerant succulent.

What is claimed is:

1. A new and distinct cultivar of *Gasteria* hybrid plant named 'WT10' as herein illustrated and described.

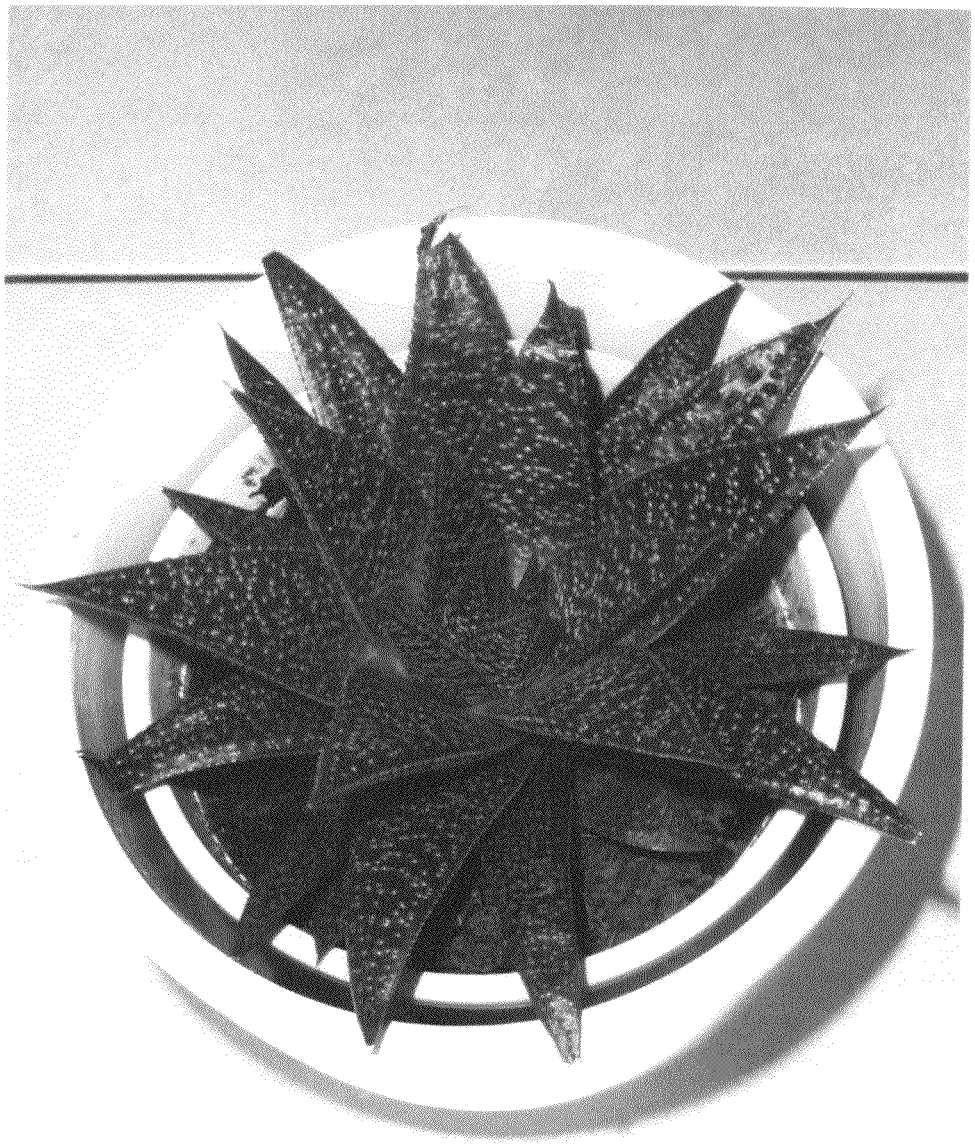

* * * * *